(12) United States Patent
Viertiö-Oja

(10) Patent No.: US 7,509,161 B2
(45) Date of Patent: Mar. 24, 2009

(54) METHOD AND APPARATUS FOR DETERMINING THE CEREBRAL STATE OF A PATIENT USING GENERALIZED SPECTRAL ENTROPY OF THE EEG SIGNAL

(75) Inventor: Hanna E. Viertiö-Oja, Espoo (FI)

(73) Assignee: Instrumentarium Corporation, Helsinki (FI)

( * ) Notice: Subject to any disclaimer, the term of this patent is extended or adjusted under 35 U.S.C. 154(b) by 649 days.

(21) Appl. No.: 10/967,030

(22) Filed: Oct. 15, 2004

(65) Prior Publication Data

US 2005/0137494 A1    Jun. 23, 2005

Related U.S. Application Data

(60) Provisional application No. 60/513,302, filed on Oct. 22, 2003.

(51) Int. Cl.
*A61B 5/04* (2006.01)
(52) U.S. Cl. .................................................. 600/544
(58) Field of Classification Search ......... 600/544–545, 600/300
See application file for complete search history.

(56) References Cited

U.S. PATENT DOCUMENTS

| | | | |
|---|---|---|---|
| 4,907,597 A | 3/1990 | Chamoun | |
| 5,010,891 A | 4/1991 | Chamoun | |
| 5,320,109 A | 6/1994 | Chamoun et al. | |
| 5,458,117 A | 10/1995 | Chamoun et al. | |
| 6,631,291 B2 * | 10/2003 | Viertio-Oja et al. | 600/544 |
| 6,658,287 B1 * | 12/2003 | Litt et al. | 600/544 |
| 6,678,548 B1 * | 1/2004 | Echauz et al. | 600/544 |
| 6,731,975 B1 * | 5/2004 | Viertio-Oja et al. | 600/544 |
| 6,801,803 B2 * | 10/2004 | Viertio-Oja | 600/544 |
| 7,228,169 B2 * | 6/2007 | Viertio-Oja et al. | 600/544 |
| 7,299,088 B1 * | 11/2007 | Thakor et al. | 600/544 |
| 7,367,949 B2 * | 5/2008 | Korhonen et al. | 600/483 |
| 2002/0173729 A1 * | 11/2002 | Viertio-Oja et al. | 600/544 |
| 2003/0055355 A1 * | 3/2003 | Viertio-Oja | 600/544 |
| 2003/0167019 A1 * | 9/2003 | Viertio-Oja et al. | 600/544 |
| 2004/0082876 A1 * | 4/2004 | Viertio-Oja et al. | 600/544 |
| 2005/0010116 A1 * | 1/2005 | Korhonen et al. | 600/481 |

OTHER PUBLICATIONS

*A Primer for EEG Signal Processing in Anesthesia*, Ira J. Rampil, M.S., M.D., Anesthesiology, vol. 89, No. 4, Oct. 1998, pp. 980-1002.

*Development Equations for the EEF*, E.R. John, H. Ahn, L. Prichep, T. Trepetin, D. Brown, and H. Kaye, Science, 10980, 210: 1255-1258.

*On the Structure of EEG Development*, A. Alvarez, P.A. Valdes, R.D. Pascual, L. Galan, R. Biscay, and J. Bosch, Electroenceph. Clin. Neurophysiol., 1989, 73: 10-19.

*Psychological and Psychophysiological States*, M. Dongier, W.C. McCallum, G. Torres, and W. Vogel, in: A. Redmond (Ed.), Handbook of Electroenceph. Clin. Neurophysiol., vol. 6A, Elsevier, Amsterdam, 1976: 195-254.

(Continued)

*Primary Examiner*—Charles A Marmor, II
*Assistant Examiner*—Navin Natnithithadha
(74) *Attorney, Agent, or Firm*—Andrus, Sceales, Starke & Sawall, LLP

(57) ABSTRACT

A method and apparatus for ascertaining the cerebral state of a patient using generalized spectral entropy of the EEG signal.

8 Claims, 14 Drawing Sheets

OTHER PUBLICATIONS

*Event-related EEG/MEG Synchronization and Desynchronization: Basic Principles*, Clinical Neurophysiology 110 (1999) pp. 1842-1857.

*Quantification of EEG Irregularity by Use of the Entropy of the Power Spectrum*, T. Inouye, K. Shinosaki, H. Sakamotor, S. Toi, S. Ukai, A. Iyama, Y. Katsuda and M. Hirano, Electroencephalography and Clinical Neurophysiology, 70 (1191) 204-210.

*Stochastic Complexity Measures for Physiological Signal Analysis*, I. A. Rezek et al., 1998 IEEE Transactions on Biomedical Engineering, vol. 45, No. 9, Sep. 1998, pp. 1186-1191.

*Approximate Entropy as an Electroencephalographic Measure of Anesthetic Drug Effect during Desflurane Anesthesia*, Jorgen Bruhn, M.D. et al., Anesthesiology, vol. 92 No. 3, Mar. 2000, pp. 715-726.

*Entropy of the EEG Signal is a Robust Index for Depth of Hypnosis*, Dr. Hanna Viertio-Oja et al., 2000 SAS Meeting Abstracts, American Society for Anesthesiologists, Oct. 14, 2000, pp. 1-2.

*New Method to Determine Depth of Anesthesia from EEG Measurements*, Dr. Hanna Viertio-Oja et al., Journal of clinical Monitoring and Computing, vol. 16, No. 1., Jan. 2000, p. 60.

*Theoretical Electroencephalogram Stationary Spectrum for a White-noise-driven Cortex: Evidence for a General Anesthetic-induced Phase Transition*, Moira I. Steyn-Ross and D.A. Steyn-Ross et al. 1999 The American Physical Society, Physical Review E, vol. 60, No. 6, Dec. 1999, pp. 7299-7310.

*Automatic analysis and monitoring of burst suppression in anesthesia*, M. Särkelä et al., Journal of Clinical Monitoring and Computing 17:125-134, 2002.

* cited by examiner

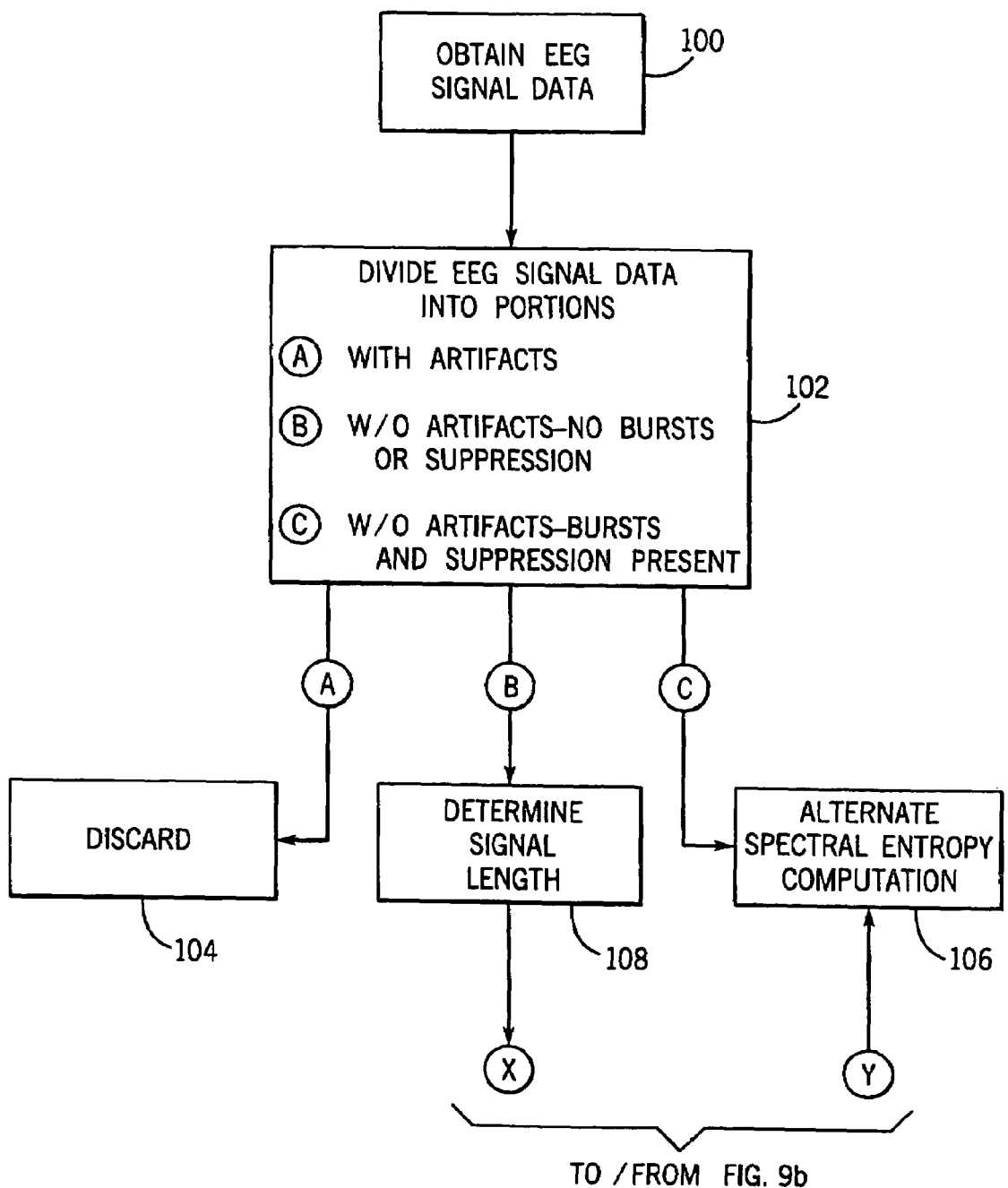

METHOD AND APPARATUS FOR DETERMINING THE CEREBRAL STATE OF A PATIENT USING GENERALIZED SPECTRAL ENTROPY OF THE EEG SIGNAL

CROSS REFERENCE TO RELATED APPLICATION

The present application claims the benefit of U.S. Provisional Application No. 60/513,302, filed Oct. 22, 2003.

BACKGROUND OF THE INVENTION

The present invention relates to a method and apparatus for determining the cerebral state of a patient using a measure of the complexity of the EEG signal, such as the spectral entropy of the signal. More particularly, the present invention relates to a method and apparatus for accurately making such determination when artifacts and/or burst suppression is present in the EEG signal through the use of a generalized spectral entropy of the EEG signal. The present invention may be used in conjunction with the teachings in earlier U.S. patent application Ser. No. 09/688,891, filed Oct. 16, 2000, now U.S. Pat. No. 6,731,975, assigned to a common assignee, which application is incorporated herein by reference.

One application of the method and apparatus of the present application is determining the extent of hypnosis of a patient resulting, for example, from the administration of an anesthetic agent. That extent is often termed the "depth of anesthesia." In a simplistic definition, anesthesia is an artificially induced state of partial or total loss of sensation or pain, i.e. analgesia. For most medical procedures the loss of sensation is accompanied by a loss of consciousness on the part of a patient so that the patient is amnestic and is not aware of the procedure. The "depth of anesthesia" generally describes the extent to which consciousness is lost following administration of an anesthetic agent.

A typical electroencephalogram, or EEG, obtained from electrodes applied to the scalp and forehead of a patient is shown in FIG. 1. A macro characteristic of EEG signal patterns is the existence of broadly defined low frequency rhythms or waves occurring in certain frequency bands. Four such bands are recognized: Delta (0.5-3.5 Hz), Theta (3.5-7.0 Hz), Alpha (7.0-13.0 Hz) and Beta (13.0-32.0 Hz). Alpha waves are found during periods of wakefulness and may disappear entirely during sleep. The higher frequency Beta waves are recorded during periods of intense activation of the central nervous system. The lower frequency Theta and Delta waves reflect drowsiness and periods of deep sleep. Even higher frequency EEG patterns than those described above have been investigated, although measurements are difficult due to very low amplitudes of these high frequency waves.

By analogy to the depth of sleep, it can be said that the frequency of the EEG will decrease as the depth of anesthesia increases, while the magnitude of the signal initially often increases. However, this gross characterization is too imprecise and unreliable to use as an indication of such a critical medical aspect as the extent of hypnosis. Further, EEG signal changes during anesthesia may not fully correlate with changes in the hypnotic state of the patient. For example, it has been reported that in a 12-18 Hz frequency band, EEG activity initially increases as anesthetic agents are administered and only thereafter decreases as anesthesia deepens.

During deep sleep or anesthesia, the EEG signal may develop a pattern of activity which is characterized by alternating periods or "bursts" of normal, or high frequency and amplitude, voltage signals and periods of low or no voltage, which periods are termed those of "suppression." See FIG. 2. The extent of this phenomenon can be expressed as a "burst suppression ratio (BSR)" which is an EEG parameter describing the time the EEG voltage is in the suppressed state as a fraction of a sampling period. The burst suppression ratio gives a rough indication of the depth of anesthesia: a high burst suppression ratio corresponding to a deeper level of anesthesia than does a low burst suppression ratio.

The limitations of direct analysis of EEG signals has led to the investigation and use of other techniques to study EEG waveforms to ascertain the underlying condition of the brain, including the depth of anesthesia to which a patient is subjected.

Some of the techniques by which EEG signals can be analyzed in an effort to determine the depth of anesthesia are well described in Ira J. Rampil, *A Primer for EEG Signal Processing in Anesthesia*, Vol. 89, Anesthesiology No. 4, pgs. 980 et seq., October 1998. Prefatory to the use of such analysis techniques, the EEG signals are typically subjected to analog to digital signal conversion by sequentially sampling the magnitude of the analog EEG signals and converting same to a series of digital data values. The sampling is typically carried out at a rate of 100 Hz or greater. The digital signals are stored in the magnetic or other storage medium of a computer and then subjected to further processing to ascertain the underlying state of the brain. Such processing typically uses sets of sequential EEG signal samples or data points representing a finite block of time, commonly termed an "epoch." The analysis of the data is usually carried out on a moving average basis employing given data points and a certain number of backward data points.

One EEG analysis technique is to examine, in some meaningful way, how the voltage of an EEG signal changes over time. Such an analysis is termed a "time-domain analysis." Because of its generally random nature, an EEG signal is not a deterministic signal. This means that it is not possible to exactly predict future values of the EEG from past values in the manner that, for example, the shapes of past QRS complexes in an ECG signal can be used to predict future values for analytical and diagnostic purposes. Thus, while certain statistical characteristics of random signals, such as an EEG, can be determined and used for analytical purposes, time-domain based EEG analysis methods have not proven greatly successful in clinical applications since the results do not behave in a completely consistent manner. Time-domain based analysis has, however, been used in the study and quantification of burst suppression in the EEG signal.

A second approach to analyzing EEG waveforms examines signal activity as a function of frequency, i.e. a "frequency-domain analysis." It has long been recognized that complex waveforms, such as EEG signals, can be decomposed, or transformed, into a plurality, or spectrum, of simple sine or cosine waves of various frequencies, amplitudes, and phases. Frequency-domain spectra can be obtained from sequential time-domain EEG signal data by a Fourier transform. Frequency-domain analysis analyzes the spectrum of frequency signals obtained from the transform to determine characteristics and features occurring in wave forms having the various frequencies of the spectrum. Several parameters relating frequency-domain EEG signal data to the hypnotic state of a patient have been developed.

For clinical use, it is desirable to simplify the results of EEG signal analysis of the foregoing, and other, types into a workable parameter that can be used by an anesthesiologist or anesthetist in a clinical setting when attending the patient. Ideally, what is desired is a simple, single parameter or index that quantifies the depth of anesthesia on a consistent, continuous scale extending from full alertness to maximally deep, but reversible, hypnosis. To be fully useful such a scale should maintain its consistency, notwithstanding the differing pharmacological effects of different anesthetic agents, as well as the differing physiologies of different patients. The scale should rapidly respond to changes in the depth of anesthesia in the patient.

In the search for such a parameter, an approach to the analysis of electroencephalographic signals that is receiving increased attention is to examine and quantify the regularity or irregularity of the highly random EEG signals. This approach is based on the premise that neuronal systems, such as those of the brain, have been shown to exhibit a variety of non-linear behaviors so that measures based on the non-linear dynamics of the EEG signal should allow direct insight into the state of the underlying brain activity.

For example, it is known that developmental factors such as maturation (John et al, *Development Equations for the EEG*, Science, 210, (1980) pgs. 1255-1258 and Alvarez et al., *On the Structure of EEG Development*, Electroenceph, Clin. Neurophysiol., 1989, 73:10-19) and attention (Dongier et al. *Psychological and Psychophysiological States* in A. Rémond (Ed), Handbook of Electroenceph. Clin. Neurophysiol., Vol. 6A, Elsevier, Amsterdam, 1976: pgs. 195-254) increase the irregularity of the EEG signal. Concentration on a particular mental task has been shown to result in a greater degree of local desynchronization of EEG (Pfurtscheller et al., *Event-related EEG/MEG Synchronization and Desynchronization: Basic Principles*, Clinical Neurophysiology 110 (1999) pgs. 1842-1857, Inoye et al. *Quantification of EEG Irregularity by use of the Entropy of the Power Spectrum*, Electro-encephalography and Clinical Neurophysiology, 79 (1991) pgs. 204-210). These findings suggest that an active cortex of the brain generally has a more irregular EEG patterns than an inactive cortex.

There are a number of concepts and analytical techniques directed to quantifying the irregularity and complex nature of random or stochastic signals such as the EEG. One such concept is entropy. Entropy, as a physical concept, is related to the amount of disorder in a physical system. When used in information theory and signal analysis, entropy addresses and describes the irregularity complexity, or unpredictability characteristics of a signal. In a simple example, a signal in which sequential values are alternately of one fixed magnitude and then of another fixed magnitude has an entropy of zero, i.e. the signal is completely regular and totally predictable. A signal in which sequential values are generated by a random number generator has greater complexity and a higher entropy.

Applying the concept of entropy to the brain, the premise is that when a person is awake, the mind is full of activity and hence the state of the brain is more complex. Since EEG signals reflect the underlying state of brain activity, this is reflected in relatively more "irregularity" or "complexity" in the EEG signal data, or, conversely, in a low level of "order." As a person falls asleep or is anesthetized, the brain function begins to lessen and becomes more orderly and regular. As the activity state of the brain changes in such circumstances, it is plausible to consider that this will be reflected in the EEG signals by a relative lowering of the "irregularity" or "complexity" of the EEG signal data, or conversely, increasing "order" in the signal data. When a person is awake, the EEG data signals will have higher entropy and when the person is asleep the EEG signal data will have a lower entropy.

With respect to anesthesia, an increasing body of evidence shows that EEG signal data contains more "order", i.e. less "irregularity", and lower entropy, at higher concentrations of an anesthetic agent, i.e. greater depth of anesthesia, than at lower concentrations. At a lower concentration of anesthetic agent, the EEG signal has higher entropy. This is due, presumably, to lesser levels of brain activity in the former state than in the latter state. See "*Stochastic complexity measures for physiological signal analysis*" by I. A. Rezek and S. J. Roberts in IEEE Transactions on Biomedical Engineering, Vol. 4, No. 9, September 1998 and Bruhn, et al. "*Approximate Entropy as an Electroencephalographic Measure of Anesthetic Drug Effect during Desflurane Anesthesia*", Anesthesiology, 92 (2000), pgs. 715-726. See also H. Viertiö-Oja et al. "*New method to determine depth of anesthesia from EEG measurement*" in J. Clin. Monitoring and Comp. Vol. 16 (2000) pg. 16 which reports that the transition from consciousness to unconsciousness takes place at a universal critical value of entropy which is independent of the patient.

The pertinence of the concept of entropy to the conscious and unconscious states of the brain is also supported in recent theoretical work (see Steyn-Ross et al., Phys. Rev. E60 1999, pgs. 7229-7311) which applies thermodynamic theory to the study of the brain. This work points to the conclusion that when a patient undergoing anesthetization passes from the conscious state to the unconscious state, a thermodynamic phase transition of the neural system of the brain takes place which is roughly analogous to the liquid-solid phase change occurring when water freezes into ice. During the process of freezing, an amount of entropy, proportional to the latent heat of the process, is removed so that water and ice have different entropies. According to the theory, the conscious and unconscious states of the brain should have distinct, different values of entropy. While thermodynamical entropy is conceptually different from the entropy in information theory, it is plausible to assume a close correlation between the two in this context. In a well-ordered, anesthetized state the neurons are obviously likely to have more regular firing patterns that are reflected in a more regular EEG signal than in the more disordered, awake state. If this theory is experimentally proven, it will lend further support to the concept of entropy as a fundamental characteristic of the cerebral state of the brain.

In sum, the following point to the advantages of EEG signal irregularity or complexity characteristics, or entropy, as in indication of the cerebral state of a patient. First, certain forms of entropy have generally been found to behave consistently as a function of anesthetic depth. See the Bruhn et al. and H. E. Viertiö-Oja et al. article "*Entropy of EEG signal is a robust index for depth of hypnosis*", Anesthesiology 93 (2000) A, pg. 1369. This warrants consideration of entropy as a natural and robust choice to characterize levels of hypnosis. Second, because entropy correlates with depth of anesthesia at all levels of anesthesia, it avoids the need to combine various subparameters in the manner described in U.S. Pat. Nos. 4,907,597; 5,010,891; 5,320,109; and 5,458,117. Third, the transition from consciousness to unconsciousness takes place at a critical level of entropy which is independent of the patient. Also, and of particular practical significance, recovery of a patient toward consciousness from anesthesia can often be predicted by a rise in entropy toward the critical level. See the Viertio-Oja et al. article in J. Clin. Monitoring and Computing.

A number of techniques and associated algorithms are available for quantifying signal irregularity, including those based on entropy, as described in the Rezek and Roberts article in IEEE Transactions on Biomedical Engineering article. One such algorithm is that which produces spectral entropy for which the entropy values are computed in frequency space. The use of spectral entropy has an advantage of computational simplicity. It also presents the possibility of looking at the contribution of phenomena in various signal frequency ranges, including those of the EEG and EMG (electromylogram), to the entropic characteristics of an indicator for depth of anesthesia.

As hereinafter noted in detail, the computation of spectral entropy as described by Rezek and Roberts is initiated by carrying out a Fourier transform of the EEG signal to obtain a power spectrum. The power spectrum is then normalized over a selected frequency region. In a summation step, the unnormalized spectral entropy corresponding to the frequency range is computed which thereafter is normalized to entropy values in a range between 1 (maximum disorder) and 0 (complete order). The computations are carried out using signal samples or epochs of constant length, for example 5 seconds of data or twelve sequential 5 second epochs (sixty seconds) of data.

The term "spectral entropy" as used herein is deemed to be that computed using the algorithm described by Rezek and Roberts unless otherwise indicated.

While possessing the advantages of computational simplicity, use of the Rezek and Roberts algorithm is attended with certain shortcomings and limitations that affect its accuracy and hence the clinical usefulness of the resulting spectral entropy depth of anesthesia indication. These shortcomings and limitations arise, in part, from the characteristics of the EEG signal data received from the patient to which the algorithm is applied. They also arise, in part, from restraints in the computational criteria under which the Rezek and Roberts calculation can be carried out to determine spectral entropy.

With respect to the EEG signals obtained from the electrodes on the scalp and forehead of the patient, FIG. 1 is a simplistic showing of such signal data. In addition to the burst suppression phenomena shown in FIG. 2, the data will typically contain anomalies or artifacts occurring from non-EEG sources external of the brain. For example, FIG. 3A shows a variation in the EEG signal caused by an eye movement. FIG. 3B shows alterations resulting from eye blinks. It will be readily appreciated that the presence of such artifacts must be taken into consideration if an accurate determination of EEG spectral entropy is to be made. A further source of artifacts occurs if the patient is subjected to electrocautery, as when sealing blood vessels cut in a surgical procedure.

In terms used in signal analysis, EEG signal data containing artifacts are said to be "non-stationary." A "stationary" signal is one in which statistical properties, such as the mean value, standard deviation, etc. remain constant even though the instantaneous values of the signal vary in an unpredictable way. A "non-stationary" signal is one for which such properties do not remain constant.

The Rezek and Roberts algorithm is one that can only be used, as such, for stationary signals which can be treated with epochs of constant length.

However, if the artifacts occur frequently in the EEG signal data, or the signal shows frequent alteration between bursts and suppression, the amount of pieces of signal that exhibit stationarity and are of a given constant length, for example, the 5 seconds duration described above, is relatively low. Therefore, if data epochs of this length are to be used for computational purposes, a relatively large amount of data must be rejected.

The relative amount of useful data can be increased by decreasing the length of the epochs used for the computations in order to capture only stationary EEG signal data. It will be readily appreciated that it is much easier to obtain data epochs 1 second long between frequent eye movements than 5 second data epochs.

However, epoch length essentially defines the frequency resolution at which the Fourier components for the spectral entropy calculation can be obtained. Specifically, the larger the time duration of the epochs, the better the frequency resolution. Consider a signal that has been sampled with a sampling frequency F, and divided into epochs of length T. The frequency components that can be evaluated under such conditions correspond to the set of frequencies $f=1/T, 2/T, 3/T \ldots, F/2$. The frequency steps $1/T$ (resolution) are thus determined by the epoch length T. For a signal that has been collected with a 400 Hz sampling frequency, an epoch length of 5 seconds gives frequency components $f=0.2$ Hz, 0.4 Hz, 0.6 Hz, ..., 200 Hz, whereas an epoch length of 1 second gives frequency components $f=1$ Hz, 2 Hz, 3 Hz, ... 200 Hz. The frequency resolution for 5 second epochs is thus 0.2 Hz whereas the frequency resolution for 1 second epochs is only 1 Hz. A frequency resolution of 0.2 Hz is typically used/desired for EEG signal analysis in order to distinguish among frequencies that correspond to physiologically distinct activity occurring in the brain. This requires 5 second data epochs which, in turn, raise the data collection problem noted above.

A further problem in connection with the use of spectral entropy to determine the depth of anesthesia occurs particularly, in very deep anesthesia, in which the EEG signal is characterized by alternating periods of "bursts" of normal, high frequency and amplitude voltage signals and periods when such signals are suppressed.

When burst suppression occurs in the EEG signal, the spectral entropy computed with the Rezek and Roberts algorithm will remain roughly constant, in contradiction to the deepening anesthesia causing the burst suppression phenomena in the EEG signal. The resulting indication of the entropic state of the brain of a patient is thus higher than it should be and the depth of anesthesia is seen as less, i.e. not as deep, as is actually occurring in the patient. This is a source of potential and serious danger to the patient since it may cause the anesthesiologist/anesthetist to administer additional anesthetic agent to an already heavily anesthetized patient.

FIGS. 4 and 5 illustrate the foregoing phenomena. In FIGS. 4 and 5, the abscissa of the graphs is time. A patient enters a state of deep anesthesia, as by the administration of an anesthetic agent, at about 35 minutes. The patient's EEG evidences burst suppression, as indicated by the rapidly increasing value of the burst suppression ratio (BSR), the BSR being the portion of time the EEG signal is in the suppressed state as a fraction of the sampling period. See FIG. 4 at 50. A typical length for the sampling period is one minute. The ordinate of FIG. 4 is scaled in the burst suppression ratio (BSR) given as a percentage (%) value. A BSR of 100% indicates that the EEG signal is in the suppressed state throughout the sampling period, i.e. for 100% of the sampling period. A BSR of zero indicates that no burst suppression is present. As shown in FIG. 4, as the effects of the anesthetic agent wear off and the depth of anesthesia decreases after the time of 35 minutes, the BSR also decreases as more bursts appear in the EEG signal. Burst suppression ceases at about 45 minutes.

FIG. 5 shows a graph of the entropy values for the patient obtained from the Rezek and Roberts computation of spectral entropy. The ordinate of FIG. 5 is scaled in normalized values of entropy. The graph of entropy 60 in FIG. 5 does not reflect the depth of anesthesia shown by the graph 50 of the BSR in FIG. 4. That is, for a depth of anesthesia following time 35 minutes in the FIGS. 4 and 5 in which the BSR approaches 100%, the hypnotic state of the brain is actually much deeper than that shown in FIG. 5. Or, stated another way, and as shown in FIG. 5, when burst suppression sets in, spectral entropy falls to a generally constant level and remains there as the BSR increases and then decreases as shown in FIG. 4.

The reasons for the phenomenon shown in FIG. 5 are as follows. As noted above, the Fourier transform is carried on a set of sequential EEG signal samples representing a finite block of time, i.e. signals of constant length such as 5 second epochs. An EEG signal of this length will typically contain alternating periods of bursts and suppression. Also, typically, the characteristic frequency fbs corresponding to this alternation between bursts and suppression is less than the lowest frequency $f_1$, of the frequency range $[f_1, f_2]$ for which the Fourier transform is computed. The lowest frequency $f_1$ used to compute spectral entropy is typically 0.5 Hz and the characteristic frequency fbs of alternation is usually below this frequency. As a result, the power spectrum obtained from the Fourier analysis of the EEG signal samples essentially includes EEG frequency components that are present during the bursts.

While low amplitudes of the power spectrum suggest that suppression is present, this information is lost in the normalization step of the Rezek et al. computation. When the entropy value is summed or integrated in the following step of the Rezek et al. computation, the resulting spectral entropy will have roughly the same value that it would have if the EEG signal had consisted of a continuous burst with no suppression at all. This accounts for the incorrectly high value of the spectral entropy shown as graph 60 in FIG. 5 during the period in which burst suppression is actually present in the EEG signal.

The foregoing problems of EEG signal data collection and spectral entropy computation have raised difficulties in implementing the use of spectral entropy computed by the Rezek and Roberts algorithm as an accurate, useful, and practical indication of the depth of anesthesia.

BRIEF SUMMARY OF THE INVENTION

A general object of the present invention is to provide an improved method and apparatus for determining the cerebral state of a patient, including the depth of anesthesia that the patient is experiencing, using the spectral entropy of the patient's EEG signal.

A more specific object of the present invention is to provide an improved method and apparatus in which an algorithm for determining entropy, such as the Rezek and Roberts algorithm, can be used with electroencephalographic signals containing artifacts. As such phenomena are commonly, or invariably, present in the EEG signal, the present invention presents a high degree of utility with respect to the practical aspects of determining entropy and depth of anesthesia. The ability to employ a straightforward technique for computing spectral entropy, such as the Rezek et al. algorithm, lends computational simplicity to the present invention further enhances this utility.

More particularly, an object of the present invention is to provide such a method and apparatus in which the manner in which the spectral entropy of the EEG signal, and hence the depth of anesthesia, is determined is generalized so as to provide an accurate indication of the anesthetic state of the patient at all levels of hypnosis, including particularly deep levels of hypnosis in which burst suppression is present in the EEG signal.

Another feature of the present invention is that it can employ EEG signal epochs of different lengths, thereby greatly improving the efficiency of data collection.

While spectral entropy computed from epochs of different lengths are not comparable because of the differences in frequency resolution noted above, the computational technique of the present invention is one that converts the spectral entropy values obtained from epochs of different lengths to a common basis. This has several significant advantages. The first, it allows the lengths of the data epochs to be chosen adaptively with respect to the characteristics of the electroencephalogram from which the EEG signal data is taken. Thus, if there are no artifacts or burst suppression in the EEG signal data, data signal lengths of a given maximum length, for example, 5 seconds may be utilized. If artifacts and/or burst suppression are present, shorter data lengths may be used to allow stationary portions of the EEG signal to be selected among the non-stationary portions containing artifacts or burst suppression. Entropy values computed from epochs other than a standard, constant length can be transformed to be comparable to those obtained using the standard, constant length by applying a transformation that is derived for this purpose from a relationship between two mathematical concepts, continuous Shannon entropy and discrete Shannon entropy. The spectral entropy computations is thus "generalized" to extend to all types of EEG signals and not just to those from which stationary signal, fixed epoch length portions can be obtained, with an attendant increase in the efficiency of EEG signal data utilization. This approach results in a much higher portion of the EEG signal data being available for use.

The present invention provides an approach that is computationally simple, and thus efficient, while at the same time providing accurate indications of spectral entropy for EEG signals as they are actually found, i.e. containing artifacts and burst suppression. The result is an efficient and accurate determination of a cerebral state, such as the depth of anesthesia, of the patient.

Various other features, objects, and advantages of the invention will be made apparent from the following detailed description and the drawings.

BRIEF DESCRIPTION OF THE SEVERAL VIEWS OF THE DRAWING

FIGS. 9a and 9b are flow charts showing one embodiment of the present invention;

DETAILED DESCRIPTION OF THE INVENTION

Computation of Spectral Entropy

Figure 1:
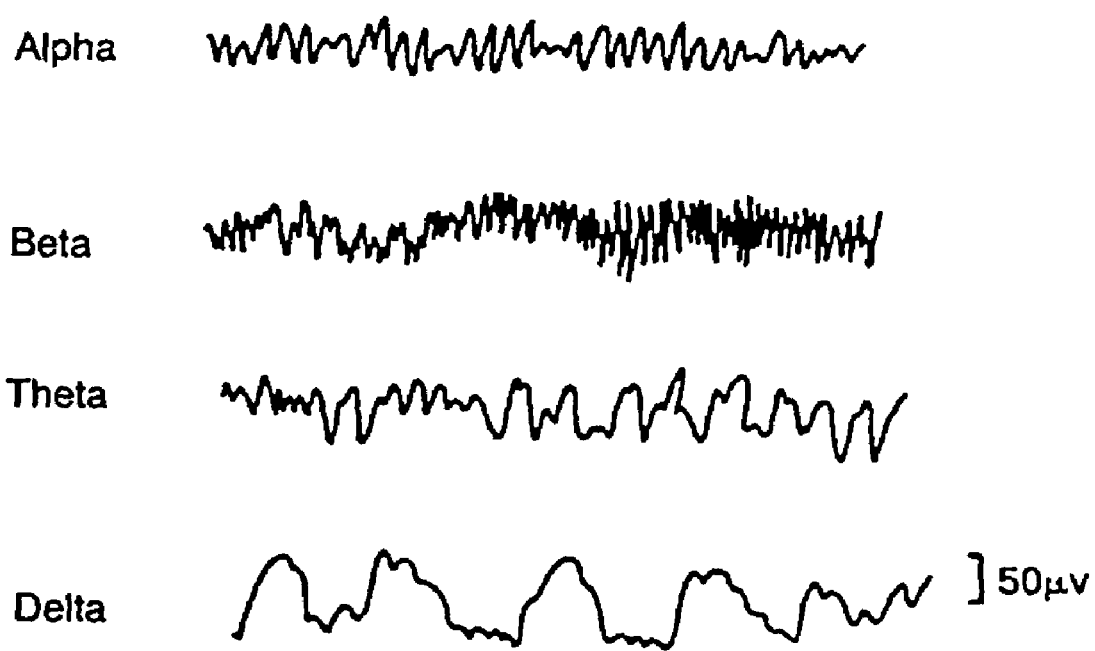
FIG. 1 shows an electroencephalogram.

The computation of the spectral entropy of a signal in the conventional manner according to Rezek and Roberts for stationary EEG signal data and constant epoch length includes the following steps.

The EEG signal is obtained from electrodes applied to the head of a patient sampled at a sampling frequency, and subjected to analog-to-digital signal conversion. The sampling frequency F is selected in accordance with the highest frequency to be evaluated and is typically around 100 Hz, Rezek et al. describing 128 Hz. The signal is low pass filtered to select the desired portion of the signal and to remove noise. Rezek et al. describe a cutoff frequency of 25 Hz as it is generally assumed that most measurable power of the EEG activity is confined to the frequency band below approximately 32 Hz. To use the Rezek and Roberts computation in the conventional manner, the filtered EEG signal is then divided into epochs of constant length. As noted above, these epochs are typically about 5 seconds in length, Rezek et al. describing epochs of 4 seconds. This will give a frequency resolution in the Fourier transform of 0.2 Hz-0.25 Hz. As noted above, the Rezek et al. computation requires signal data exhibiting stationarity.

Computation of the spectral entropy of a signal according to Rezek and Roberts includes four steps. The first is the power spectrum calculation. The Fourier transform $X(f_i)$ of the signal $x(t_i)$ is computed by the fast Fourier transform technique (FFT). The power spectrum $P(f_i)$ is calculated by squaring the amplitudes of each element $X(f_i)$ of the Fourier transform:

$$P(f_i) = X(f_i) * X^\wedge(f_i) \qquad (1)$$

where $X^\wedge(f_i)$ is the complex conjugate of the Fourier component $X(f_i)$ and '*' denotes multiplication.

The power spectrum is then normalized. The normalized power spectrum $P_n(f_i)$ is computed by setting a normalization constant $C_n$ so that the sum of the normalized power spectrum over the selected frequency region $[f_1, f_2]$ is equal to one:

$$\sum_{f_i=f_1}^{f_2} P_n(f_i) = C_n \sum_{f_i=f_1}^{f_2} P(f_i) = 1 \qquad (2)$$

In the summation step, the spectral entropy corresponding to the frequency range $[f_1, f_2]$ is computed as a sum $$S[f_1, f_2] = \sum_{f_i=f_1}^{f_2} P_n(f_i) \log\left(\frac{1}{P_n(f_i)}\right) \qquad (3)$$

Thereafter, the entropy value is normalized to range between 1 (maximum irregularity) and 0 (complete regularity). The value is divided by the factor $\log(N[f_1, f_2])$ where $N[f_1, f_2]$ is equal to the total number of frequency components in the range $[f_1, f_2]$:

$$S_N[f_1, f_2] = \frac{S[f_1, f_2]}{\log(N[f_1, f_2])} \qquad (4)$$

Spectral Entropy as an Indication of Depth of Anesthesia

FIG. 6 shows, as a function of time, values of entropy as computed above for a patient receiving an anesthetic agent as compared to a more conventional measure of the depth of anesthesia.

Figure 6A:
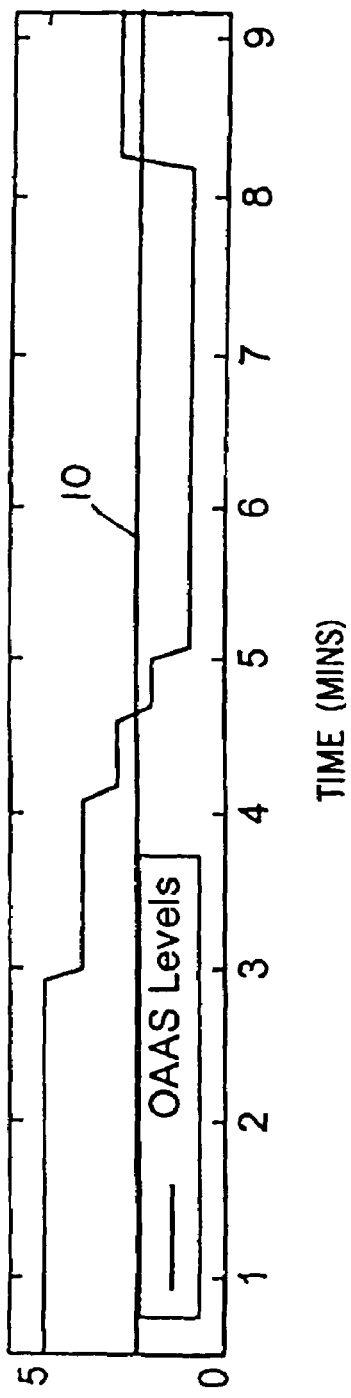
FIGS. 6a and 6b are graphs showing values of entropy as compared to the conventional OAAS scale for a patient receiving an anesthetic agent.

FIG. 6a indicates the depth as determined by an anesthesiologist attending the patient using various physical stimuli, i.e. an observers assessment of alertness and sedation, or OAAS. At an OAAS level 5, the patient is fully awake whereas at the OAAS level 0 corresponds to a deep state of anesthesia in which the patient shows no response to tetanic stimulation. Horizontal line 10 indicates a level at which transition from the conscious to unconscious state is deemed to take place, i.e. between OAAS level 3 and OAAS level 2.

In the example shown in FIG. 6a, the attending anesthesiologist considers a patient undergoing anesthetization to have moved from OAAS level 5 to OAAS level 4 at about three minutes. At about four minutes, the patient is deemed to have dropped to OAAS level 3.

Thereafter, at about four and a half minutes, the patient is deemed to have lost consciousness as by failing to respond to verbal commands and the loss of the eyelid reflex. This is evidenced in the change from level 3 to below level 2 and the crossing of horizontal line 10.

Figure 6B:
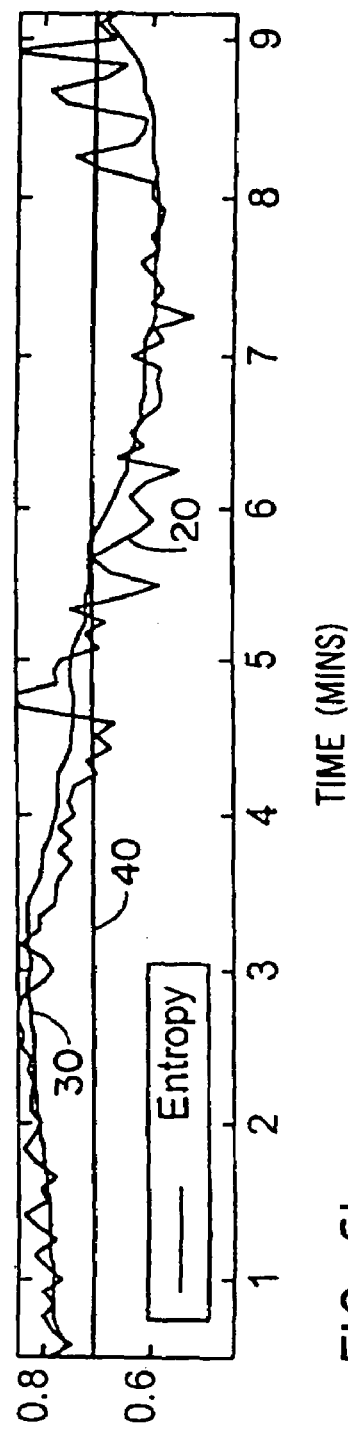

FIG. 6b shows a value of spectral entropy computed from 5 seconds of data as graph 20 and a value of spectral entropy computed as median values of twelve sequential 5 second epochs (sixty seconds) of data as graph 30. As can be seen from FIG. 6b, as the consciousness of the patient decreases from the commencing of monitoring, both graphs 20 and 30 similarly decrease and cross horizontal line 40 which identifies the entropy level that characterizes the transition from the conscious state to the unconscious state.

With respect to the emergence from the unconscious state, in the example shown in FIG. 6, the patient regains consciousness at about 8 minutes.

It will be seen from FIG. 6b that graphs 20 and 30 follow, and provide an accurate indication of, the emergence of the patient to the state of consciousness, also as shown on the OAAS scale.

Figure 7A:
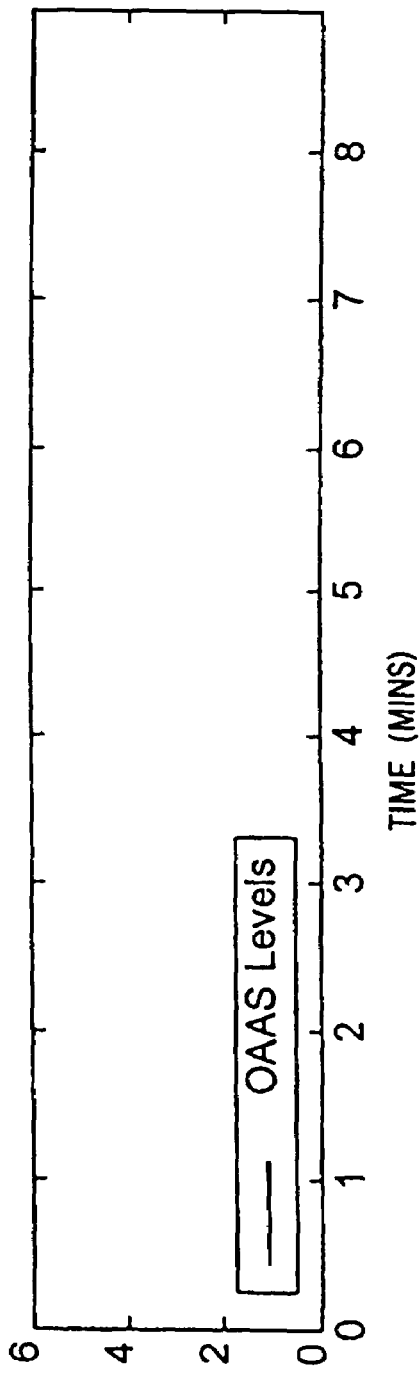
FIGS. 7a and 7b are graphs showing values of entropy of a patient at surgical levels of anesthesia.
Figure 7B:
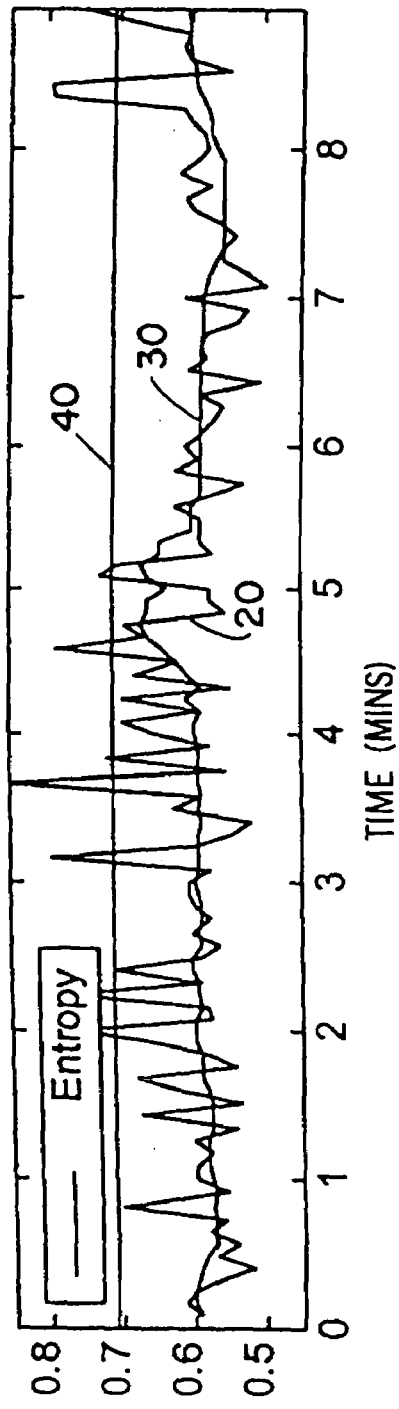

FIGS. 7a and 7b show the values of entropy at surgical levels of anesthesia, i.e. when the OAAS scale is zero as shown in FIG. 7a. Horizontal line 40 in FIG. 7b is the same as horizontal line 40 in FIG. 6b and comprises the entropic value forming the borderline between the conscious and unconscious states.

Figure 8A:
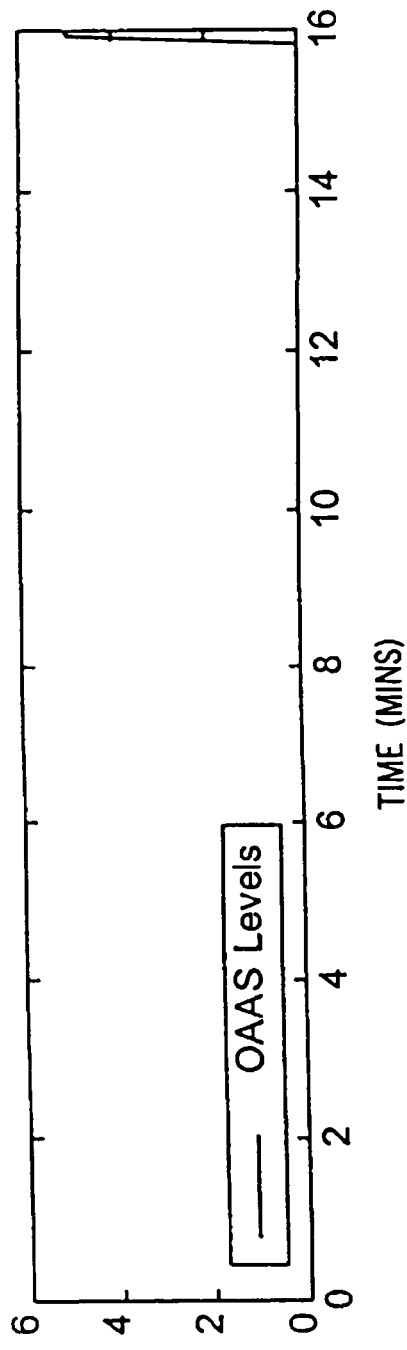
FIGS. 8a and 8b are graphs showing values of entropy as compared to the conventional OAAS scale for a patient emerging from anesthesia.
Figure 8B:
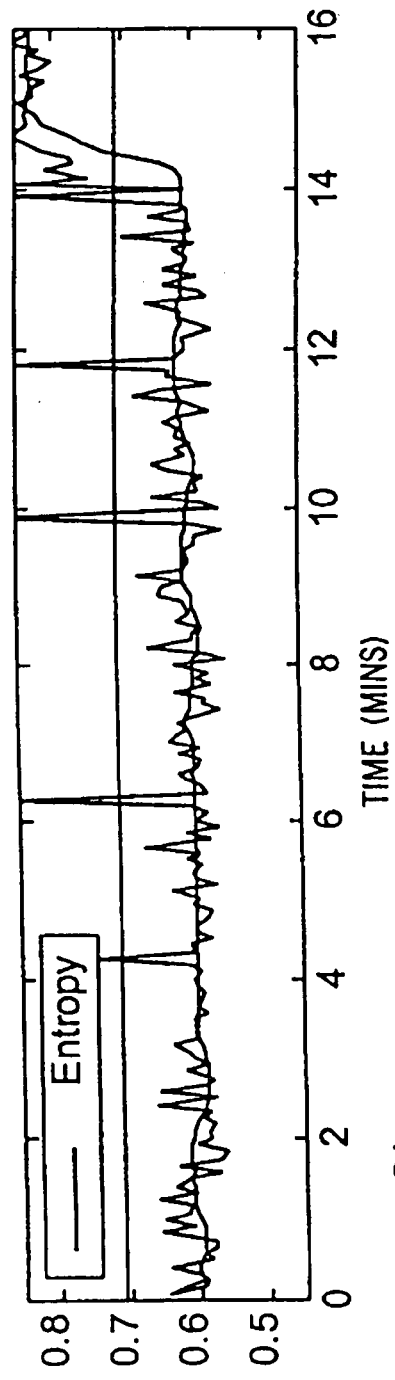

FIGS. 8a and 8b show a recovery of a patient from surgical levels of anesthesia to consciousness. The rise in the values of entropy at about 14 minutes, informs the anesthesiologist of the approaching recovery to the conscious state and even before the anesthesiologist becomes aware of the recovery from the OAAS criteria. See FIG. 8a.

FIGS. 6 through 8 thus clearly show the use and advantages of the spectral entropy of the EEG signal as a measure of the depth of anesthesia.

Computation of Generalized Spectral Entropy

The foregoing conventional use of the Rezek et al. spectral entropy computation is difficult when artifacts are present in the EEG signal data due to data acquisition problems. Burst suppression phenomena may be present in the EEG signal to exacerbate the data acquisition problem and to raise the accuracy problem shown in FIG. 5.

The gist of the present invention is to provide a method and apparatus for computing the spectral entropy of the EEG signal in a generalized manner that is both accurate and can use data epochs of different lengths, thereby to lessen, and ideally eliminate, data acquisition problems.

Figure 9B:
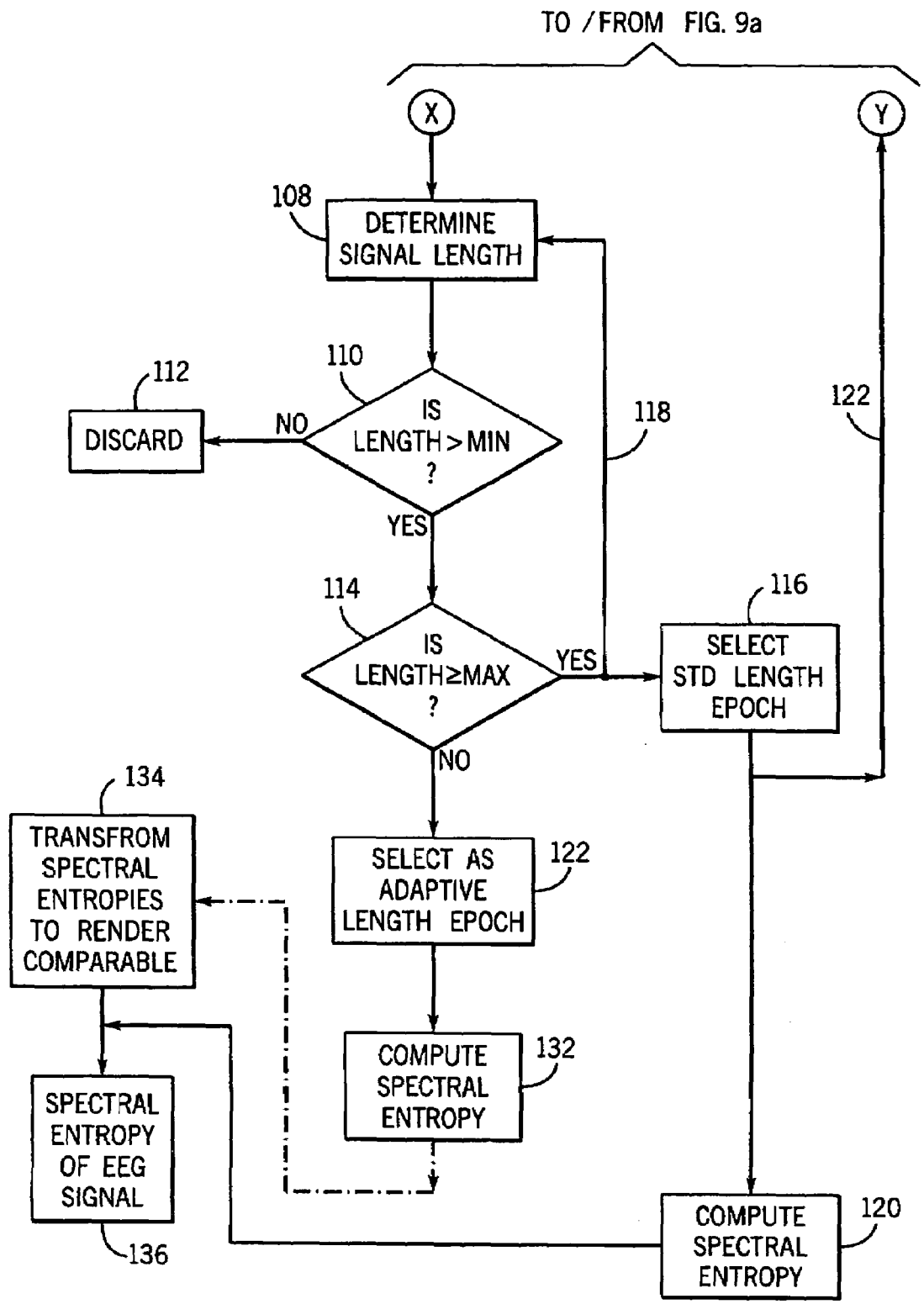

In the approach of the present invention shown in the flow chart of FIG. 9, the EEG signal data is obtained from the patient in step 100 at a desired sampling frequency, digitized, and bandpass filtered in the manner described above. The EEG signal data is analyzed at steps 102 and 104 to divide the EEG signal data into portions in accordance with the presence or absence of artifacts and burst and suppression phenomena.

Figure 2:
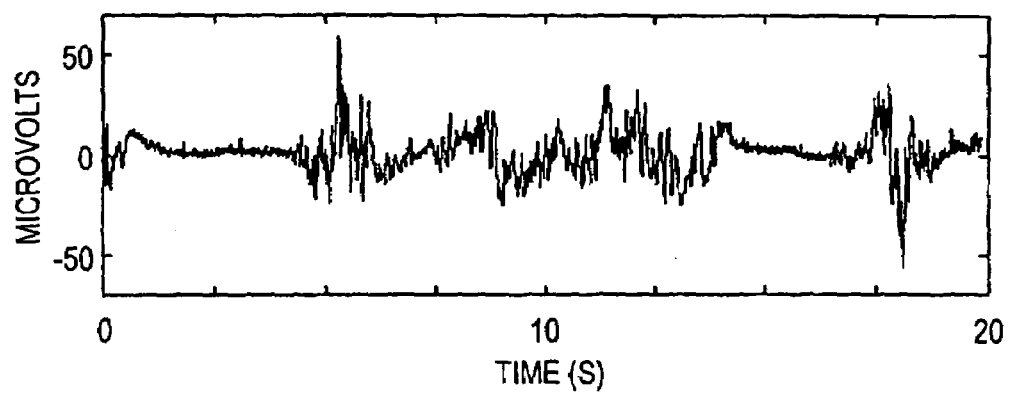
FIG. 2 shows an electroencephalographic signal in which burst suppression is present.
Figure 3A:
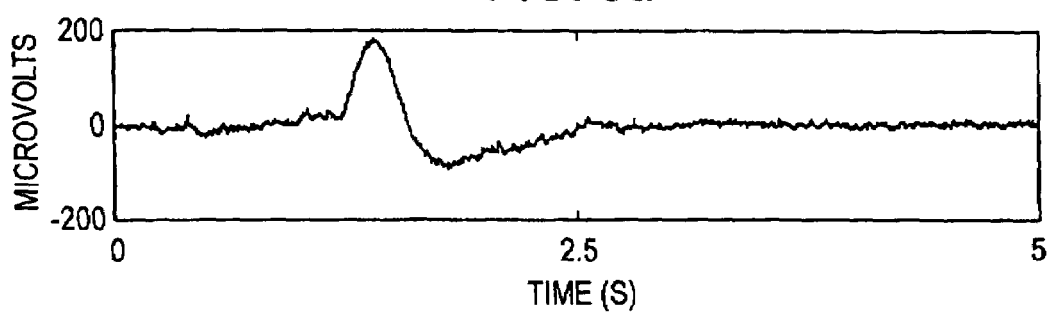
FIGS. 3A and 3B show artifacts in an EEG signal.
Figure 3B:
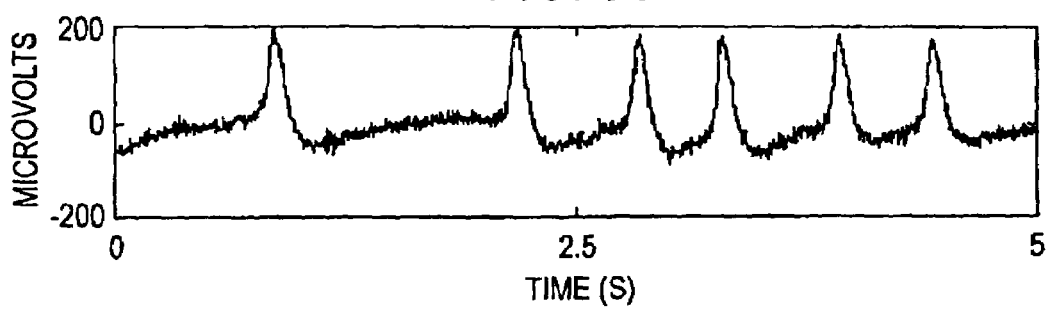

The determination of the presence of artifacts and/or burst suppression in the EEG signal data in step 102 may be carried out using conventional signal analysis techniques for analyzing the forms of the EEG signal shown in FIG. 2 and FIG. 3. See for example E. Niedermeyer and F. Lopes da Silva (1999): Electroencephalography. Basic principles, clinical applications and related fields 4. Ed., Williams & Wilkins, Baltimore, USA.

Portions of the EEG signal data containing artifacts, shown as (A) in FIG. 9, are discarded at step 104. Portions of the remaining EEG signal data, i.e. the portions without artifacts, are further divided into those in which burst suppression is present (portion C) and those in which burst suppression is not present (portion B). Portion B represents a normal, or stationary, EEG signal, i.e. no artifacts or burst/suppression phenomena. If only burst suppression is present in the EEG signal, the spectral entropy of these portions can be determined in the manner shown in FIGS. 12 and 13 and described below. This is shown by reference numeral 106 in FIG. 9.

The length of the artifact free portions (B) of the EEG signal data will vary since they are dependent on the presence or absence of artifacts in the signal data.

The length of the portions (B) of the artifact-free signal data, i.e. the stationary portions of the signal data, is determined at step 108. If the length of the signal portion is less than a minimum length, for example 0.5 seconds, the signal portion is discarded at steps 110 and 112. If the length of the signal portion is greater than a maximum signal length for a selected epoch length, for example, 5 seconds, as determined at step 114, the standard length epoch is selected from the signal data at step 116 and the process is repeated as indicated by the line 118 for the remaining portion of the signal to determine the possible existence of further epochs of standard length.

For epochs of standard length, for example 5 seconds, as determined at step 116, the spectral entropy for these epochs is determined in the conventional manner using the Rezek et al. algorithm described in the preceding portion of the text. This occurs at step 120.

If the length of the EEG signal data portion determined at steps 110 and 114 is greater than the minimum length but less than the standard length, this portion is determined as an adaptive length epoch, i.e. the length, is adapted to the amount of stationary data available in an EEG signal. The adaptive selection of epoch length in step 122 will result in epochs having differing lengths smaller than the standard length.

Next, the normalized, discrete spectral entropy of the adaptive length epochs is determined at step 132. This is performed by applying the algorithm by Rezek and Roberts, using the set of frequency values $f=1/T, 2/T, 3/T \ldots, F/2$ that are determined by the particular epoch length T and sampling frequency F.

The entropy values computed from epochs of different lengths are not directly comparable to each other. A transformation in order to make them comparable can, however, be derived by applying a particular mathematical theorem that relates the concept of discrete entropy to a concept of continuous entropy. Discrete entropy refers to an entropy that is computed over discrete points, such as the spectral entropy by Rezek and Roberts. In information theory, a continuous entropy refers to an entropy that is instead defined by a continuous integral.

$$S_{cont} = -\int_0^{f_{lim}} P_n(f) \log P_n(f) df \qquad (5)$$

where $P_n(f)$ is a normalized continuous power spectrum that satisfies the normalization condition $$\int_0^{f_{lim}} P_n(f) df = 1 \qquad (6)$$

and $f_{lim}$ is the upper-band limit of the spectrum (it is assumed that $P_n(f)=0$ for $f>f_{lim}$).

Steyn-Ross (D. A. Steyn-Ross, Ph.D. Thesis, Waikato University, Hamilton, New Zealand (2002)) showed that continuous spectral entropy Scont can be estimated by a discrete histogram spectral entropy $S_{hist}$, which can be defined by $$S_{hist} = -\Delta f \sum_{i=1}^{N} P_n(f_i) \log(P_n(f_i)) \qquad (7)$$

where the discrete power spectrum values $P_n(f_i)$ have been normalized by $$\sum_{i=1}^{N} P_n(f_i) \Delta f = 1 \qquad (8)$$

$\Delta f$ corresponds to the discrete frequency resolution, and N is the number of discrete frequency values. If $f_{max}$ denotes the maximum frequency up to which the entropy is computed, then $N=f_{max}/\Delta f$. The normalization constraint essentially means that the histogram, consisting of histograms bins with height $P_n(f_i)$ and width $\Delta f$, has a unit area. Steyn-Ross also showed that the histogram spectral entropy $S_{hist}$ is related to the discrete spectral entropy S computed for the corresponding frequency resolution $\Delta f$ by a linear relation:

$$S = S_{hist} - \log(\Delta f) \qquad (9)$$

In this invention, Equation (9) is applied to derive a transformation to relate spectral entropies computed using different epoch lengths to each other. First, the discrete spectral entropy normalized to range between 0 and 1 can be obtained from $$S^{norm} = \frac{S}{\log(N)} = \frac{S_{hist} - \log(\Delta f)}{\log(N)} \quad (10)$$

Next, a transformation between spectral entropies computed from epochs of different adaptive lengths in step 132 is established at step 134 in order to render the entropies comparable. The normalized spectral entropy computed from epoch of length $T_1$, with frequency resolution $1/T_1$ is denoted, as $S_{T1}^{norm}$.

Similarly, spectral entropy computed from epoch of length $T_2$, with frequency resolution $1/T_2$, is denoted by $S_{T2}^{norm}$. Using the Equation (10) above, we can relate these entropies to the histogram spectral entropy $S_{hist}$ by $$S_{T1}^{norm} = \frac{S_{hist} - \log\left(\frac{1}{T_1}\right)}{\log(f_{max}T_1)} \quad (11)$$

and $$S_{T2}^{norm} = \frac{S_{hist} - \log\left(\frac{1}{T_2}\right)}{\log(f_{max}T_2)} \quad (12)$$

By eliminating $S_{hist}$, we obtain $$S_{T2}^{norm} = \frac{\log(f_{max}T_1)}{\log(f_{max}T_2)} S_{T1}^{norm} + \frac{\log\left(\frac{T_2}{T_1}\right)}{\log(f_{max}T_2)} \quad (13)$$

Using the transformation of Equation (13), entropy values can be computed for the particular adaptive epoch length, and then transformed to be accurately representative for that of any given epoch length, such as a standard length epoch. This permits epochs of differing lengths to be obtained from the EEG signal data between artifacts and periods of suppression and then transformed to the given epoch length for use in providing the spectral entropy complexity of the EEG signal data in step 136 as shown in FIGS. 6, 7, and 8. For example, for the computation of spectral entropy up to a maximum frequency of 32 Hz, the transformation from a 1 second adaptive length epoch ($T_1$) to a standard length 5 second epoch ($T_2$) would be:

$$S_{T2}^{norm} = \frac{\log(32 \text{ Hz} \times 1 \text{ s})}{\log(32 \text{ Hz} \times 5 \text{ s})} S_{T1}^{norm} + \frac{\log\left(\frac{5 \text{ s}}{1 \text{ s}}\right)}{\log(32 \text{ Hz} \times 5 \text{ s})} \quad (14)$$

The steps of the method are repeated for subsequent portions of the EEG signal data to provide a graph, such as those shown in FIGS. 6, 7, and 8 for use in determining the depth of anesthesia of a patient.

Through its ability to use EEG signal data epochs of differing adaptive lengths, the method of the present invention minimizes the amount of EEG signal data that must be discarded because of the presence of artifacts while at the same time providing an accurate indication of the complexity of the EEG signal data and the depth of anesthesia of the patient.

In a highly efficacious, practical embodiment of the invention, the standard length data epochs determined to be standard in step 116 would proceed in the normal computational manner described in the preceding section of this specification leaving only data epochs that were not of the standard length, to proceed through transformation step 134.

Figure 10:
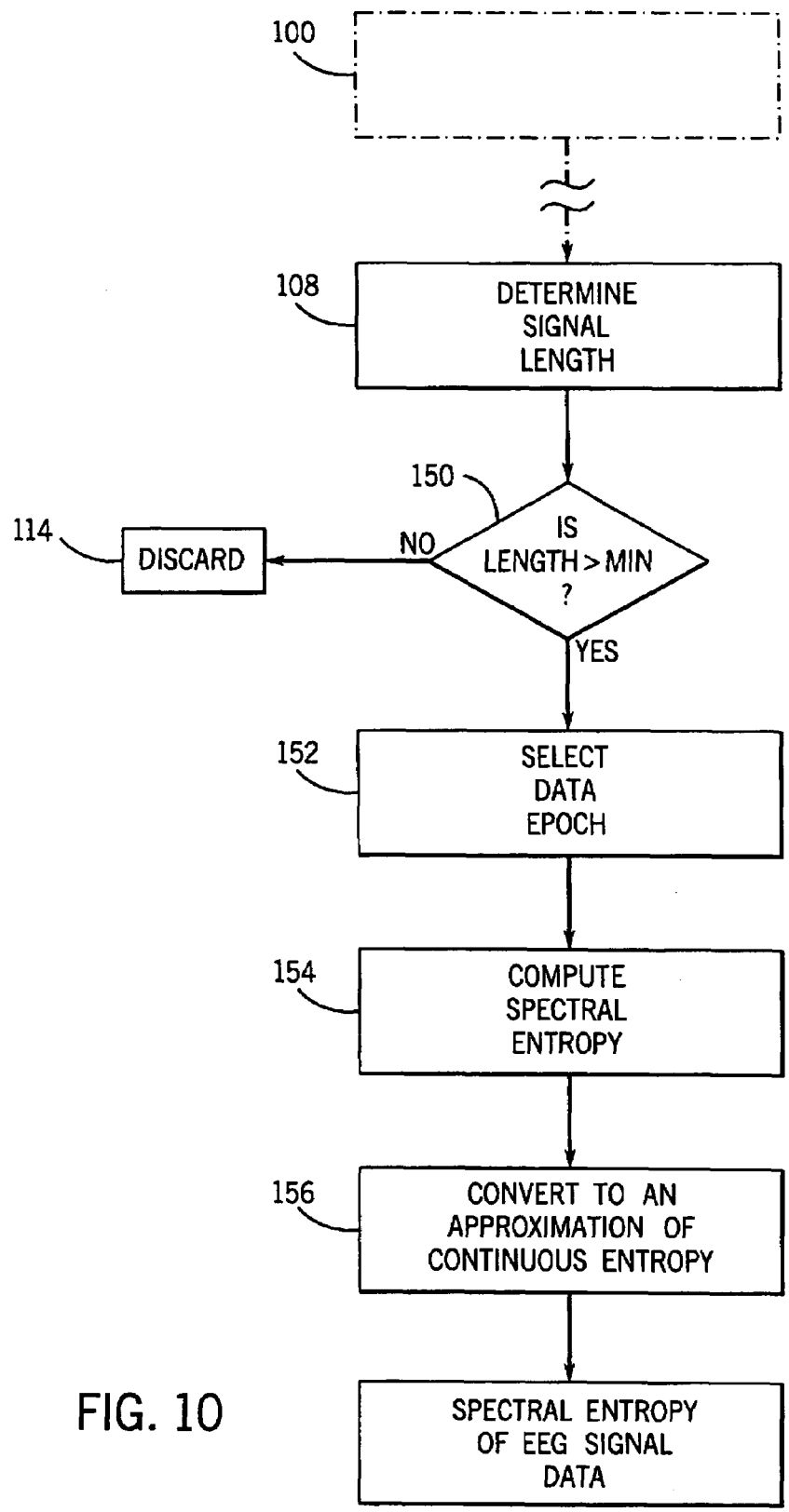
FIG. 10 is a flow chart showing another embodiment of the present invention.

While the above described technique possesses the practical advantages noted above, in that it need be applied only to epochs of non-standard length, it is also possible to carry out the computation of spectral entropy on a continuous frequency basis as outlined in FIG. 10. As shown diagrammatically in FIG. 10, steps 100 through 108 are the same. In steps 150 and 152, all data epochs greater than a minimum length are selected for further use in the computation. The spectral entropy of each of these segments of the EEG signal data is computed using the computation of Rezek et al. and Roberts in step 154. Equation (10) is then applied to convert from the Rezek et al. spectral entropy ($S^{norm}$) to the histogram spectral entropy $S_{hist}$ which provides an approximation of continuous entropy in step 156. $S_{hist}$ is only an approximation of continuous spectral entropy because it is not possible to have an infinitely long sample to compute the continuous spectral entropy.

As before, the foregoing steps are repeated for subsequent segments of EEG signal data to provide a graph such as those shown in FIGS. 6, 7, and 8 for use in determining the depth of anesthesia of the patient.

Alternative Computation when Burst Suppression Present in EEG Signal

Figure 4:
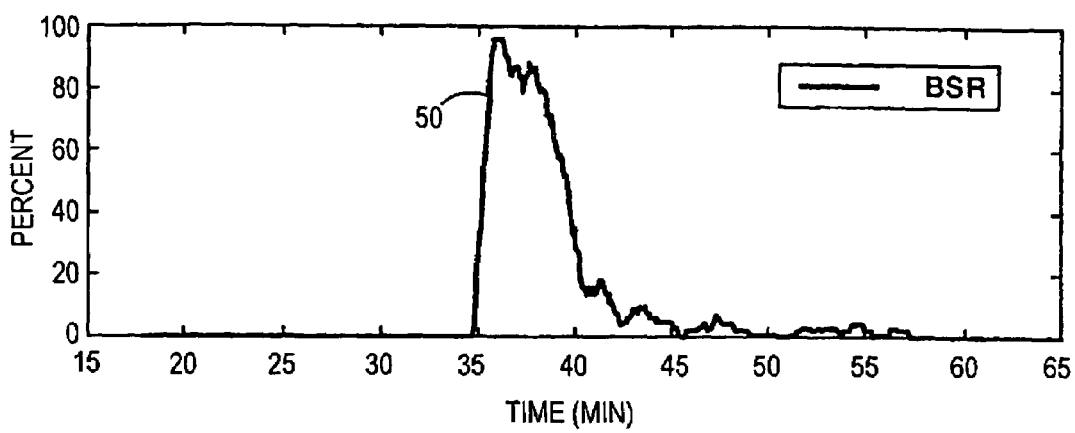
FIG. 4 is a graph of the burst suppression ratio of a patient receiving an anesthetic agent.
Figure 5:
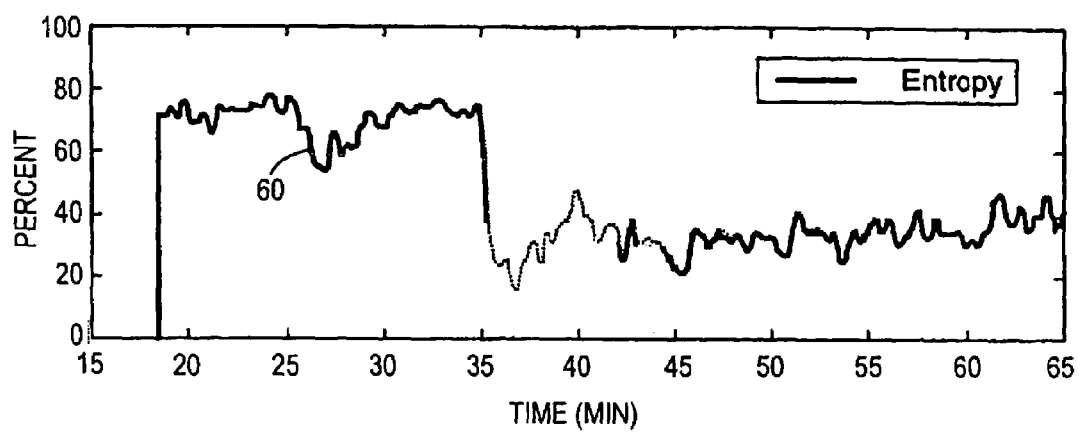
FIG. 5 is a graph of an EEG signal spectral entropy for the same patient as shown in FIG. 5 obtained by the method of Rezek et al.

As shown in FIGS. 4 and 5, the computation of Rezek and Roberts produces incorrectly high values for spectral entropy in the deep levels of anesthesia associated with the phenomenon of burst suppression. In the following, methods to obtain entropy values that consistently reflect the hypnotic state of the patient are described.

Prefatory to an understanding of these methods, it must be appreciated that spectral entropy is not an additive quantity. That is, the entropy of an epoch that is two seconds long is not equal to the sum of the entropies of the two one second epochs. However, for the analysis of EEG signal data during suppression of the EEG signal, it is nonetheless advantageous to define an additive concept. This can be termed entropy content $\Delta S$ corresponding to a time unit $\Delta t$. An entirely plausible assumption is that the entropy content within the periods of suppression is equal to zero, i.e. the suppressed subepochs are considered perfectly regular. The total entropy for a given length epoch, such as a standard length epoch, can then be computed by adding together the entropy contents $\Delta S$ within the standard length epoch.

In the following, two techniques to obtain spectral entropy based on the foregoing concept are described in detail. The first one is mathematically more rigorous, whereas the second approach provides a more simple approximative technique that is often sufficiently accurate.

Figure 12A:
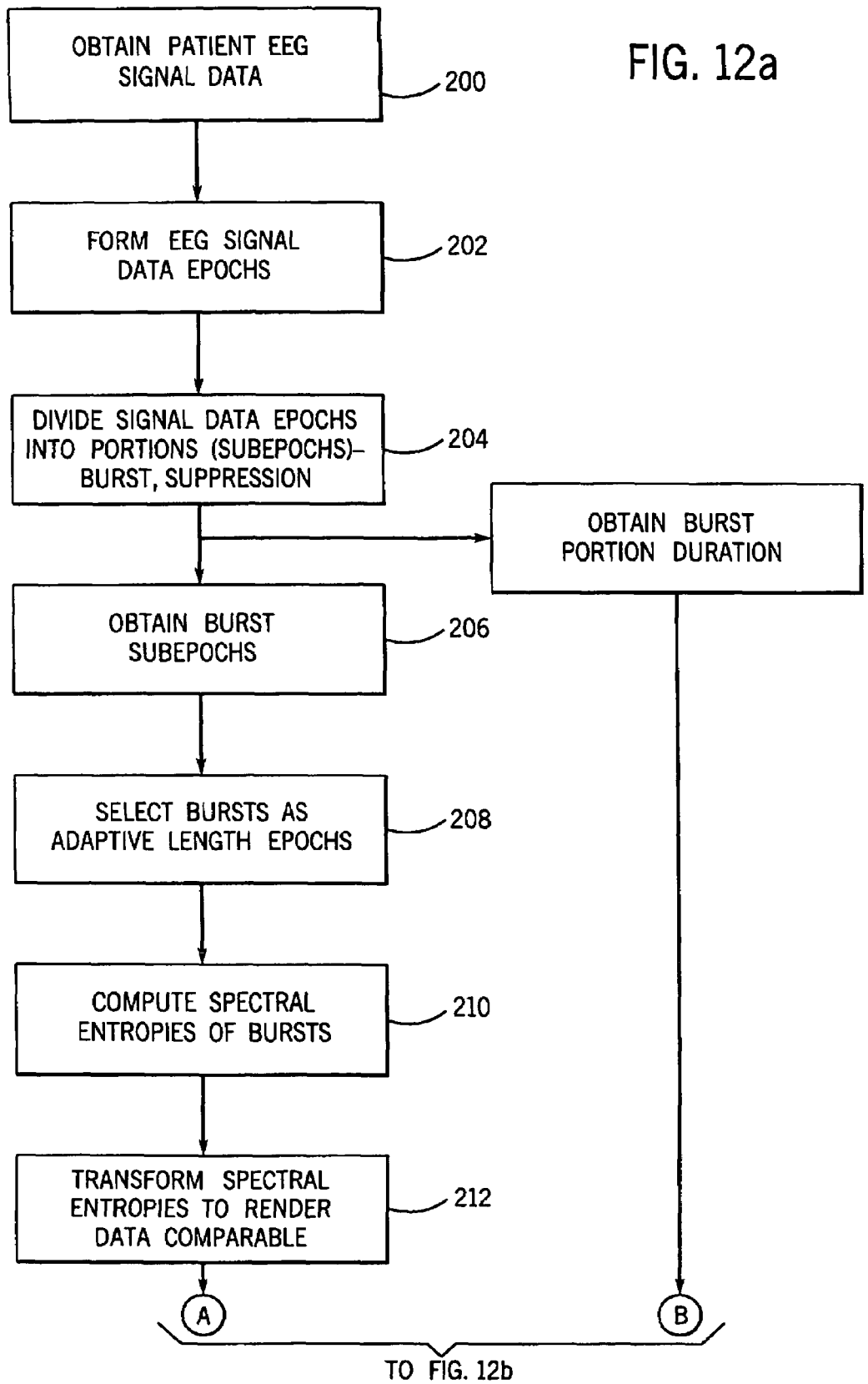
FIGS. 12a and 12b are flow charts showing the further embodiment of the present invention.
Figure 12B:
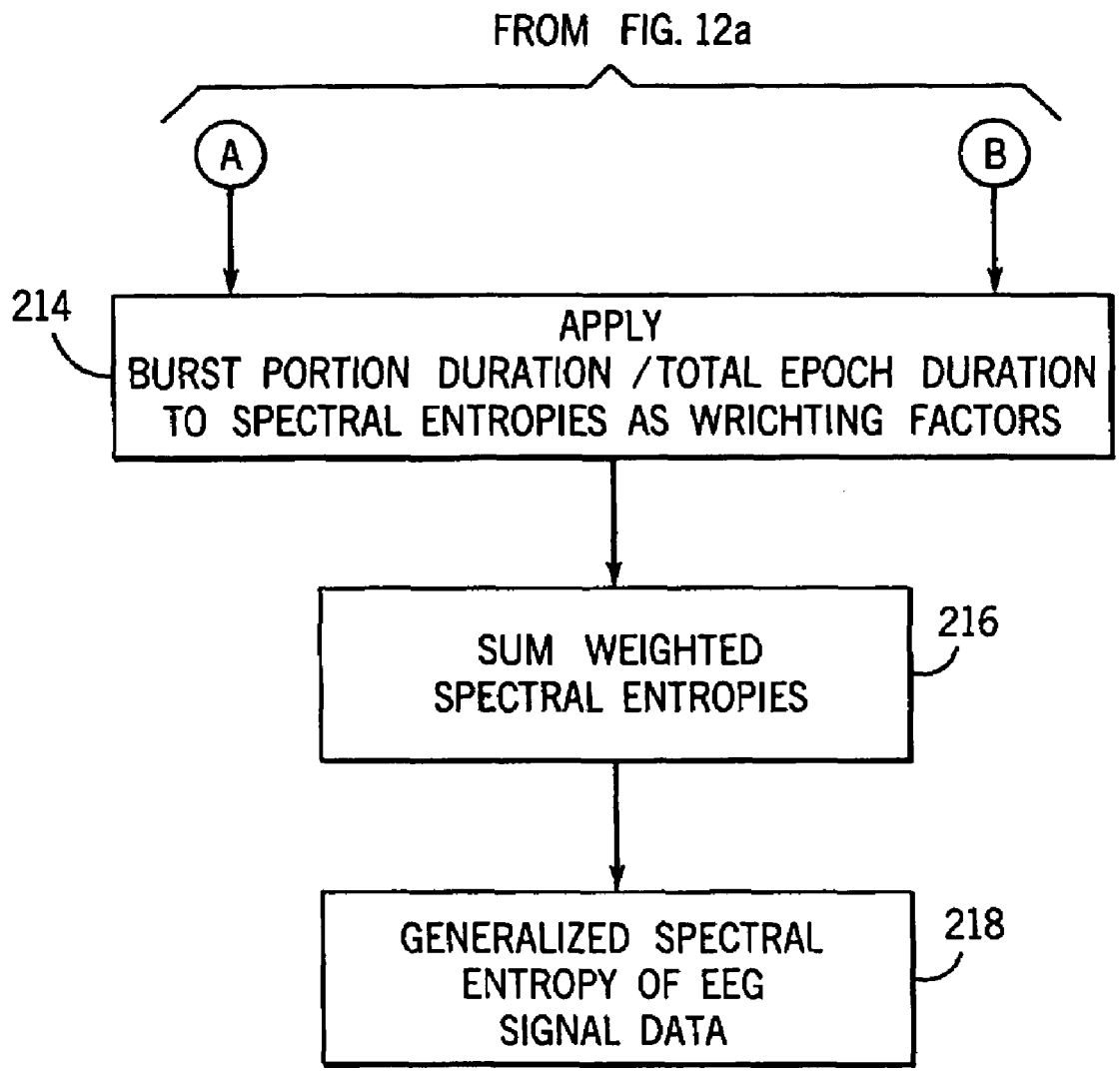

FIG. 12 describes the more rigorous technique. In this approach the EEG signal obtained at step 200 is formed into epochs at step 202. The epochs are then divided into portions that include only bursts or only suppression at step 204. For example, assume spectral entropy is to be computed using epochs of 5 seconds as formed in step 202. The typical duration of a burst is between 0.5 and 10 seconds, and of a suppression between 1 second and several minutes. A standard epoch may thus contain only burst signal, only suppression phenomena, or both alternating with each other. In step 204, each epoch is divided into sequential subepochs $e_1 \ldots e_N$ with durations $\Delta t_1 \ldots \Delta t_N$ so that subepochs $e_1, e_3, e_5, \ldots$ contain only burst signal data and subepochs $e_2, e_4, e_6, \ldots$ contain only suppression signal data.

The subepochs $e_1 \ldots e_N$ containing burst signal are obtained at step 206 and selected as adaptive length epochs at step 208.

The spectral entropy $S_1$ for each subepoch $e_1, e_3, e_5, \ldots$ containing the bursts is first computed in step 210 using the Rezek et al. algorithm. It is next transformed in step 212 to be comparable to the entropy values obtained using the standard epoch length by applying the transformation defined by Equation (13). The computation is carried out for all burst subepochs $e_1, e_3, e_5, \ldots$ to obtain entropy values $S_1, S_3, S_5, \ldots$. The corresponding entropy values of the suppression subepochs $e_2, e_4, e_6, \ldots$ are equal to zero. Each subepoch now contributes to the total entropy of the epoch an entropy content equal to $\Delta S_i = S_i \Delta t_i / t_{total}$, so that the spectral entropy of the complete epoch is computed at steps 214, 216, 218 as $$S_{total} = \Sigma_i (S_i \Delta t_i) / t_{total} \quad (15)$$

The sum corresponds to a weighted average of the entropies $S_i$ of the subepochs, with the relative lengths $\Delta t_i / t_{total}$ of the subepochs as weighting factors.

Figure 11:
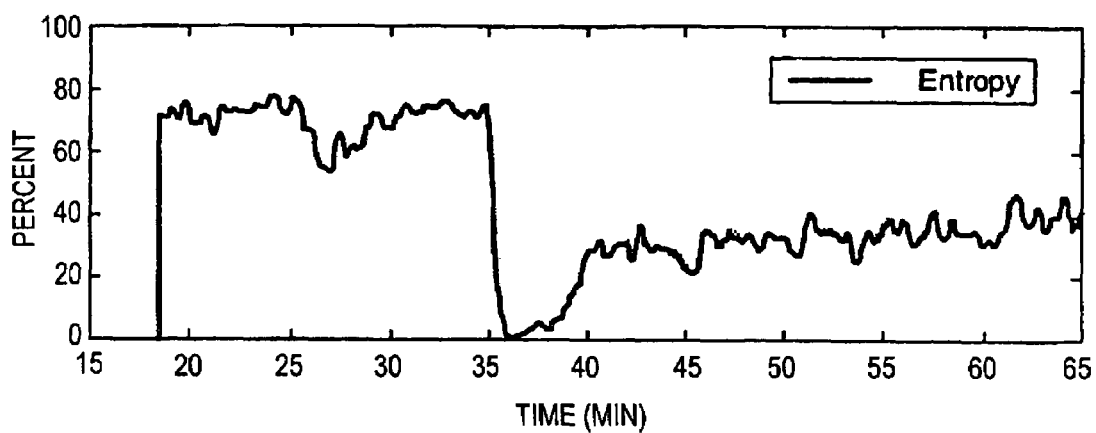
FIG. 11 is a graph showing spectral entropy during burst suppression computed in accordance with a further embodiment of the present invention.

The result is the graph 70 shown in FIG. 11. As can be seen from a comparison of FIG. 7 to FIGS. 4 and 5, the result of applying this technique of the present invention is a lowering of the value of the spectral entropy to correctly indicate the deepening anesthesia that is characterized by the burst suppression. In particular, when burst suppression ratio reaches the value of 100%, corresponding to total suppression and a perfectly regular EEG signal, entropy goes consistently to zero.

Figure 13:
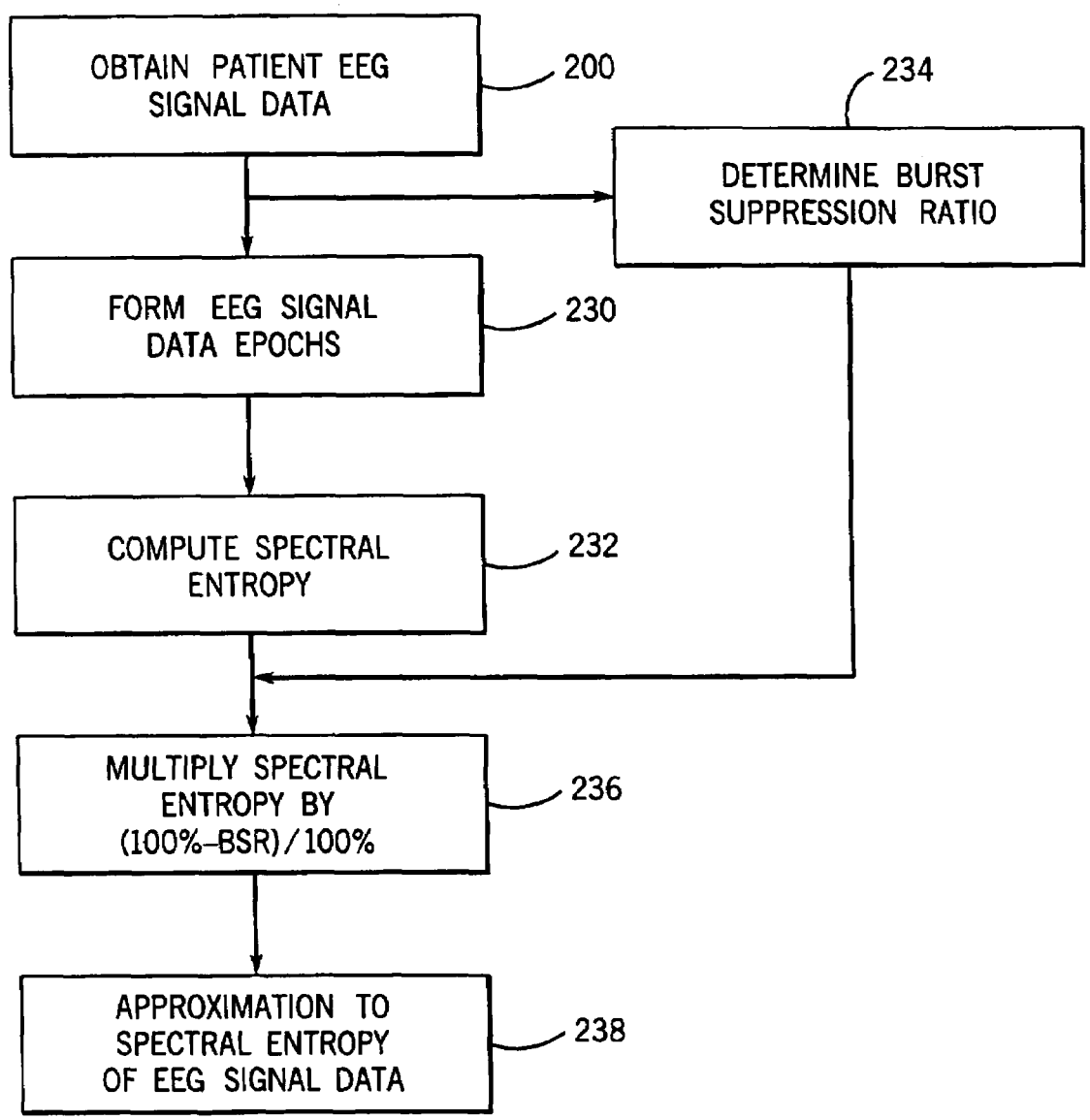
FIG. 13 is a flow chart showing a modification of the further embodiment of the present invention.

An approximate way to take into account burst suppression in the entropy computations is shown in the flow chart of FIG. 13. In this approach, the patient EEG signal data is obtained at step 200 and formed into epochs at step 230. The spectral entropy of each epoch of the data is computed at step 232. The patient signal data is also analyzed at step 234 to obtain the burst suppression ratio (BSR). Suitable, reliable techniques for BSR-computations have been presented in the literature (see, for example, M. Särkelä et al., *Automatic analysis and monitoring of burst suppression in anesthesia*, Journal of Clinical Monitoring and Computing 17: 125-134, 2002).

Assuming the characteristic frequency of alternation between burst and suppression ($f_{bs}$) is less than the lowest frequency ($f_1$) of the frequency range used for entropy computations, typically 0.5-0.8 Hz, the frequency spectrum of an epoch essentially includes the frequency components of the bursts, and the amplitudes of these components of the spectrum are automatically weighted by the relative lengths of the subepochs in the epoch. Subepochs with suppression do not contribute to the spectrum so that if the spectral entropy of an epoch is computed using the Rezek et al. algorithm, the resulting entropy value $S_{Rezek}$ is roughly equal to a value that one would obtain for an epoch with similar burst subepochs and no suppression subepochs at all. The notion that suppression epochs should not contribute any entropy can be taken into account by scaling the entropy value with the relative duration of the bursts, so that the total spectral entropy of the epoch can be computed at step 236 as $$S_{total} = \Sigma_{ii} (S_{Rezek} t_i) / t_{total} = S \Sigma_i t_i / t_{total} = S_{Rezek} \times (100\% - BSR)/100\% \quad (16)$$

In applying Equation (16), if there is no burst suppression, the generalized spectral entropy obtained in step 238 is the same as that computed by the method of Rezek and Roberts. If some burst suppression is present, the generalized spectral entropy will be less than that computed by the method of Rezek and Roberts, as seen from a comparison of FIGS. 5 and 11. If there is total burst suppression, the generalized spectral entropy is zero.

It should be noted that Equation (16) is an approximative way to compute the spectral entropy value. The alternation between subepochs containing burst and suppression slightly distorts the spectra and affects the entropy values. In most practical cases, however, the approximate technique will give values in good agreement with the more accurate method.

Apparatus

Figure 14:
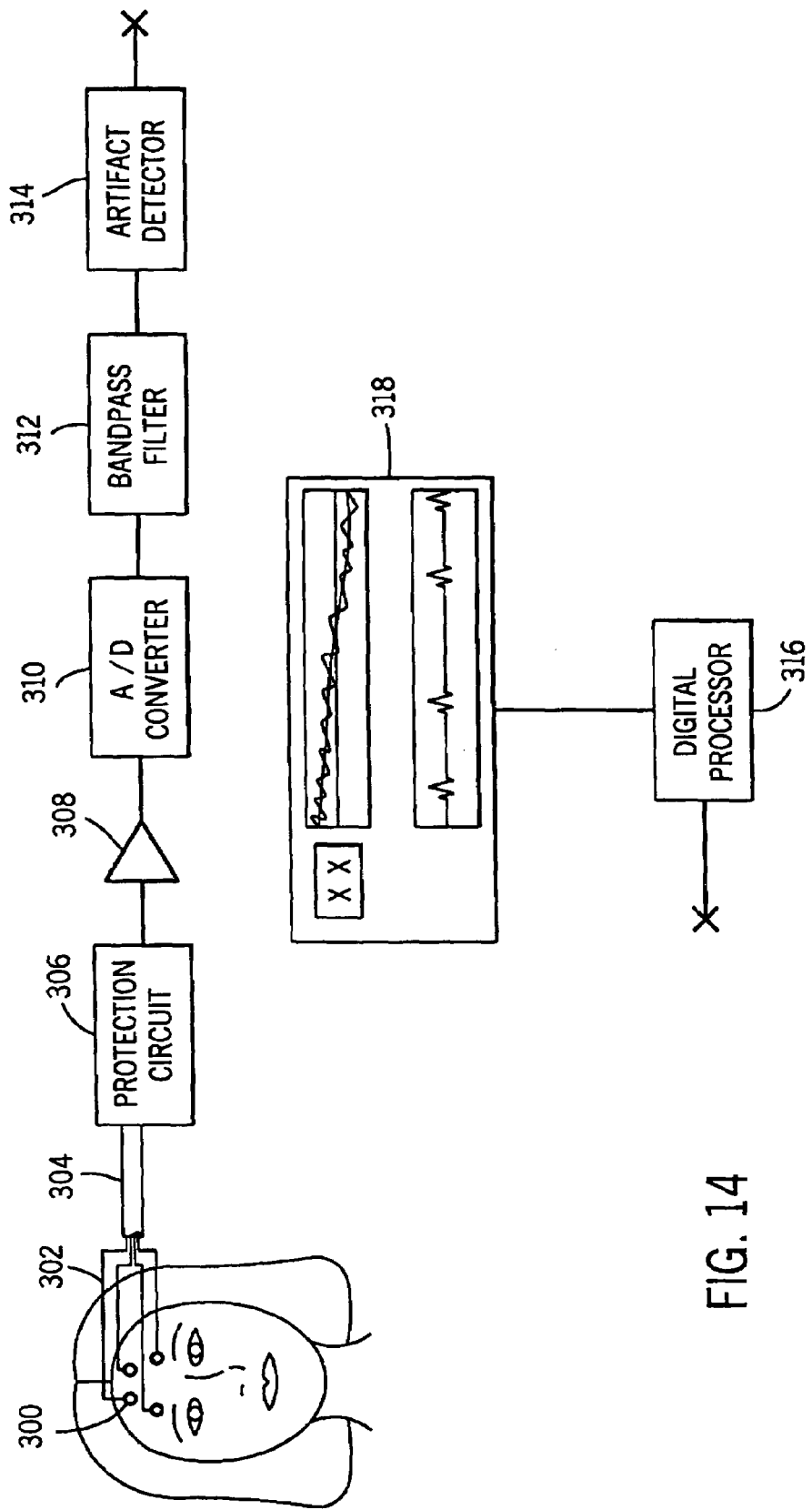
FIG. 14 shows apparatus for carrying out the present invention.

Apparatus for carrying out the present invention is shown in FIG. 14. Electrodes 300 are applied to the head of the patient in a desired manner. At least one pair and usually a plurality of pairs of electrodes are utilized. The biopotentials appearing in the electrodes are received in conductors 302 and are collected into patient cable 304.

Cable 304 connects conductors 302 to protection circuit 306 which is operative in the event the patient is subjected to electro-surgery or cardiac defibrillation. Electro-surgery employs alternating current at radio frequencies, typically between 300 and 3000 Hz to cut tissue and cauterize bleeding blood vessels. A defibrillator delivers a short current pulse to arrest arrhythmia in the heart muscle. Either of these occurrences will significantly affect the signals in conductors 302 and signals, and the purpose of protection of circuit 306 is to reject signals containing such occurrences from further use in the following portions of the circuitry.

The output of protection circuit 306 is amplified by amplifier 308 and subjected to analog to digital conversion in analog/digital converter 310. Thereafter the signals are provided to bandpass filter at filter 312 that removes noise and line frequency harmonics from the signals. The output from bandpass filter 312 is connected to artifact detector 314. While artifact detector 314 detects and removes considerable portions of the artifacts, other portions remain in the EEG signal data that is used to compute spectral entropy. The output of artifact detector 314 is connected to computational unit 316 which carries out the steps of the methods described above and produces an output of generalized spectral entropy in display 318. Or, the information may be presented in display 318 in numerical form. Display 318 may also display other physiological data, such as electrocardiographic data, breath rate, pulse, blood pressure, etc., obtained from other monitors.

Also, while artifact detector 314 is shown to illustrate removal of artifacts, the presence of artifacts can also be dealt with in the signal processing occurring in computational unit 316.

The invention has been described above in connection with cerebral states induced by the administration of an anesthetic agent. However, it will be appreciated that the method and apparatus may be used in connection with other physiological conditions which are reflected in EEG signal data obtained from a patient and with drugs other than anesthetic agents. It is therefore recognized that other equivalents, alternatives, and modifications in addition to those expressly stated, are possible and within the scope of the appended claims.

The invention claimed is:

1. A method for determining a generalized spectral entropy of EEG signal data obtained from a patient, said method comprising the steps of:

obtaining sequential EEG signal data from a plurality of electrodes applied to the patient;

obtaining portions of the EEG signal data in which the signal is stationary in nature;

determining an epoch length for the portions of the EEG signal so obtained;

comparing the determined epoch length to a standard epoch length;

for the portions of the EEG signal data so obtained, computing the spectral entropy of the EEG signal data;

for the portions of the EEG signal data having an epoch length different from the standard epoch length, transforming the computed spectral entropy to that for an EEG signal portion having the standard epoch length; and displaying the computed spectral entropy of the EEG signal data, wherein the displayed computed spectral entropy is indicative of a depth of anesthesia for the patient.

2. The method according to claim 1 wherein the transforming step is further defined as obtaining the discrete, normalized spectral entropy of the EEG signal data of the portion and as transforming the discrete normalized spectral entropy to the comparable basis form.

3. The method according to claim 2 further defined as repeating the steps of obtaining stationary EEG signal data, computing the spectral entropy, and transforming the spectral entropy.

4. The method according to claim 1 wherein the transforming step is further defined as transforming the spectral entropy so computed to an approximation of continuous spectral entropy.

5. The method according to claim 4 further defined as repeating the steps of obtaining stationary EEG signal data, computing the spectral entropy, and transforming the spectral entropy.

6. The method according to claim 1 further defined as repeating the steps of obtaining stationary EEG signal data, computing the spectral entropy, and transforming the spectral entropy.

7. The method according to claim 1 further including the steps of using portions of stationary EEG signal data having only at least a minimal length.

8. The method according to claim 1 wherein the step of computing the spectral entropy of the EEG signal comprises:

conducting a fast Fourier transform on the EEG signal data;

calculating the power spectrum for each element of the Fourier transform;

normalizing the power spectrum;

computing the spectral entropy from the power spectrum; and normalizing the spectral entropy.

* * * * *